(12) United States Patent
Akahori

(10) Patent No.: US 10,910,101 B2
(45) Date of Patent: Feb. 2, 2021

(54) IMAGE DIAGNOSIS SUPPORT APPARATUS, IMAGE DIAGNOSIS SUPPORT METHOD, AND IMAGE DIAGNOSIS SUPPORT PROGRAM

(71) Applicant: FUJIFILM Corporation, Tokyo (JP)

(72) Inventor: Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/546,769

(22) Filed: Aug. 21, 2019

(65) Prior Publication Data

US 2020/0075154 A1 Mar. 5, 2020

(30) Foreign Application Priority Data

Aug. 29, 2018 (JP) ................. 2018-159918

(51) Int. Cl.
*G16H 30/40* (2018.01)
*G06F 3/14* (2006.01)
(Continued)

(52) U.S. Cl.
CPC ............ *G16H 30/40* (2018.01); *G06F 3/14* (2013.01); *G06K 9/6215* (2013.01);
(Continued)

(58) Field of Classification Search
CPC ...... G06F 3/14; G06K 9/6215; G06K 9/6228; G06K 2209/05; G06T 3/0068; G06T 5/00; G06T 7/00; G06T 7/0014; G06T 7/38; G06T 11/00; G06T 15/08; G06T 15/205; G06T 2207/10072; G06T 2207/20084; G06T 2207/30004; G06T 2207/30016; G16H 30/20; G16H 30/40; G16H 50/20
(Continued)

(56) References Cited

U.S. PATENT DOCUMENTS 5,995,108 A * 11/1999 Isobe ................. G09G 1/06
345/421
2008/0212854 A1* 9/2008 Fukatsu ............. G06F 19/321
382/128
(Continued)

FOREIGN PATENT DOCUMENTS

JP 2008200139 A 9/2008
JP 2011036684 A 2/2011

*Primary Examiner* — Sae Won Yoon
(74) *Attorney, Agent, or Firm* — Studebaker & Brackett PC

(57) ABSTRACT

An image diagnosis support apparatus includes: an acquisition unit that acquires a plurality of first image data groups and a plurality of second image data groups to be subjected to comparative interpretation; an association unit that associates each of the plurality of first image data groups and each of the plurality of second image data groups with each other based on a degree of similarity between the image data groups; an image extraction unit that extracts a corresponding image corresponding to at least one target image of the first image data group from a second image data group among the plurality of second image data groups associated with a first image data group among the plurality of first image data groups; and a display controller that displays a set of images of the target image and the corresponding image on a display unit in a contrastable layout.

20 Claims, 13 Drawing Sheets

(51) Int. Cl.
    *G16H 50/20*    (2018.01)
    *G06K 9/62*    (2006.01)
    *G16H 30/20*    (2018.01)

(52) U.S. Cl.
    CPC ........... *G06K 9/6228* (2013.01); *G16H 30/20* (2018.01); *G16H 50/20* (2018.01)

(58) Field of Classification Search
    USPC ........................................................ 345/619
    See application file for complete search history.

(56) References Cited

U.S. PATENT DOCUMENTS

| | | | | |
|---|---|---|---|---|
| 2013/0198687 | A1* | 8/2013 | Bird | A61B 5/7435 |
| | | | | 715/810 |
| 2016/0093048 | A1* | 3/2016 | Cheng | G06K 9/6289 |
| | | | | 382/131 |
| 2016/0140738 | A1* | 5/2016 | Asaka | G01S 15/8995 |
| | | | | 382/131 |
| 2017/0154416 | A1* | 6/2017 | Dargis | G06T 7/0016 |
| 2020/0035350 | A1* | 1/2020 | Sullivan | G06N 20/00 |

\* cited by examiner

EXAMPLES OF EXAMINATION AND SERIES

EXAMINATION: ABDOMINAL CT

SERIES 1: NON-CONTRAST CT
    SERIES 2: CONTRAST CT (ARTERIAL PHASE)
    SERIES 3: CONTRAST CT (PORTAL VEIN PHASE)
    ...

EXAMINATION: HEAD MRI

SERIES 1: DIFFUSION WEIGHTED IMAGE
    SERIES 2: ADC MAP
    SERIES 3: FLAIR IMAGE
    ...

IMAGE DIAGNOSIS SUPPORT APPARATUS, IMAGE DIAGNOSIS SUPPORT METHOD, AND IMAGE DIAGNOSIS SUPPORT PROGRAM

CROSS REFERENCE TO RELATED APPLICATIONS

The present application claims priority under 35 U.S.C. § 119 to Japanese Patent Application No. 2018-159918 filed on Aug. 29, 2018. The above application is hereby expressly incorporated by reference, in its entirety, into the present application.

BACKGROUND

Technical Field

The present disclosure relates to an image diagnosis support apparatus, an image diagnosis support method, and an image diagnosis support program.

Related Art

In recent years, in the field of medical imaging, image capturing apparatuses (hereinafter, referred to as modalities) using various techniques, such as an X-ray imaging apparatus, a computed tomography (CT) apparatus, an ultrasound (US) diagnostic apparatus, a magnetic resonance imaging (MRI) apparatus, a positron emission tomography (PET) apparatus, and a single-photon emission computed tomography (SPECT) apparatus, are used. With advances in the performance of such modalities, such as speed increase and multi-slice support, a plurality of parts of a subject is imaged in one series (a plurality of pieces of image data per imaging unit acquired by each modality), so that it is possible to acquire hundreds to thousands of high-resolution tomographic images.

On the other hand, a comparative interpretation has been performed from the past in which a plurality of medical images are displayed on a display device, such as a liquid crystal display, and interpretation is performed while comparing the images. For example, by displaying a medical image of a current examination of a subject and a medical image of a past examination and performing comparative interpretation, it is possible to check the degree of progress of a lesion or detect an abnormality at an early stage. However, which tomographic image of which series is to be displayed on which screen in the case of actually performing interpretation is based on the screen operation by the user. For this reason, in the case of comparing the current examination with the past examination, the user takes time and effort to select a series or tomographic images for easy interpretation.

Therefore, in order to facilitate such comparative interpretation, various techniques for displaying a medical image on a display device have been proposed. As a specific method of display, for example, JP2008-200139A discloses a technique for generating and displaying thumbnail images showing combination information of current series image data and past series image data relevant thereto with reference to object data including image acquisition conditions at the time of examination and specific information for specifying other series image data relevant to the examination. In addition, JP2011-036684A discloses a technique for selecting a slice image, which has a region change rate in which a difference between a region change rate in a slice image at the second imaging time and a region change rate in each slice image included in a slice image group at the first imaging time is within a predetermined range, from the slice image group at the first imaging time and displaying the selected slice image and a slice image at the second imaging time.

However, for example, in a series acquired in a relatively old past examination, the object data described above may not be present or may not be standardized. In the series in which the object data described above is not present or not standardized, it is not possible to appropriately refer to the object data. Accordingly, it is not possible to appropriately associate a series to be subjected to comparative interpretation. For this reason, it is difficult to apply the technique described in JP2008-200139A. In the case of the technique described in JP2011-036684A, it is possible to match the slice positions between slice images. However, JP2011-036684A does not describe a method of matching between image data groups configured to include a plurality of slice images, that is, series.

SUMMARY

The disclosure has been made in view of the aforementioned circumstances, and an object of the disclosure is to make it possible to appropriately associate sets of series to be subjected to comparative interpretation and to extract corresponding images between the associated sets of series and display the extracted corresponding images in a contrastable layout.

An image diagnosis support apparatus according to the disclosure comprises: an acquisition unit that acquires a plurality of first image data groups and a plurality of second image data groups to be subjected to comparative interpretation from a data storage unit in which a plurality of image data groups each including a plurality of images are stored for each unit examination; an association unit that associates each image data group of the plurality of first image data groups with each image data group of the plurality of second image data groups based on a degree of similarity between each of the plurality of first image data groups and each of the plurality of second image data groups acquired by the acquisition unit; an image extraction unit that extracts a corresponding image corresponding to at least one target image of a first image data group from a second image data group, which is any image data group among the plurality of second image data groups associated with the first image data group, which is any image data group among the plurality of first image data groups, by the association unit; and a display controller that displays a set of images of the target image and the corresponding image on a display unit in a contrastable layout.

In the image diagnosis support apparatus according to the disclosure, the image extraction unit may extract the corresponding image for all the target images included in the plurality of first image data groups.

In the image diagnosis support apparatus according to the disclosure, the display controller may display sets of images of all of the target images and the corresponding images.

In this case, the display controller may display sets of the images in parallel on a screen of the display unit, or may display sets of all the images on a screen of the display unit so as to be switched one by one.

In the image diagnosis support apparatus according to the disclosure, the image data groups may be volume data configured to include a plurality of slice images, and the association unit may perform association based on a degree of similarity between pieces of pixel data of the volume data.

In the disclosure, "pixel data" refers to a collection of pixels forming an image.

In the image diagnosis support according to the disclosure, the association unit may perform association based on a feature amount in a region including a specific anatomical structure included in each of the image data groups.

In the disclosure, the "specific anatomical structure" is a specific structure forming a subject, such as the spinal cord or the heart, for example.

In the image diagnosis support according to the disclosure, the association unit may have a learned model on which machine learning has been performed so as to output whether or not combinations of input image data groups based on input of any image data group among the plurality of first image data groups and any image data group among the plurality of second image data groups correspond to each other.

In the image diagnosis support apparatus according to the disclosure, the image extraction unit may extract the corresponding image based on a degree of similarity between the target image and each image of the second image data group.

In the image diagnosis support according to the disclosure, the plurality of first image data groups and the plurality of second image data groups may be image data groups acquired by imaging the same subject at different imaging times.

An image diagnosis support method according to the disclosure comprises: acquiring a plurality of first image data groups and a plurality of second image data groups to be subjected to comparative interpretation from a data storage unit in which a plurality of image data groups each including a plurality of images are stored for each unit examination; associating each image data group of the plurality of first image data groups with each image data group of the plurality of second image data groups based on a degree of similarity between each of the plurality of first image data groups and each of the plurality of second image data groups; extracting a corresponding image corresponding to at least one target image of a first image data group from a second image data group, which is any image data group among the plurality of second image data groups associated with the first image data group, which is any image data group among the plurality of first image data groups; and displaying a set of images of the target image and the corresponding image on a display unit in a contrastable layout.

In addition, a program causing a computer to execute the image diagnosis support method according to the disclosure may be provided.

Another image diagnosis support apparatus according to the disclosure comprises: a memory that stores commands to be executed by a computer; and a processor configured to execute the stored commands. The processor executes: a step of acquiring a plurality of first image data groups and a plurality of second image data groups to be subjected to comparative interpretation from a data storage unit in which a plurality of image data groups each including a plurality of images are stored for each unit examination; a step of associating each image data group of the plurality of first image data groups with each image data group of the plurality of second image data groups based on a degree of similarity between each of the plurality of first image data groups and each of the plurality of second image data groups; a step of extracting a corresponding image corresponding to at least one target image of a first image data group from a second image data group, which is any image data group among the plurality of second image data groups associated with the first image data group, which is any image data group among the plurality of first image data groups; and a step of displaying a set of images of the target image and the corresponding image on a display unit in a contrastable layout.

According to the image diagnosis support apparatus, the image diagnosis support method, and the image diagnosis support program of the disclosure, it is possible to appropriately associate sets of series to be subjected to comparative interpretation and to extract corresponding images between the associated sets of series and display the extracted corresponding images in a contrastable layout.

DETAILED DESCRIPTION

Figures 1, 2:
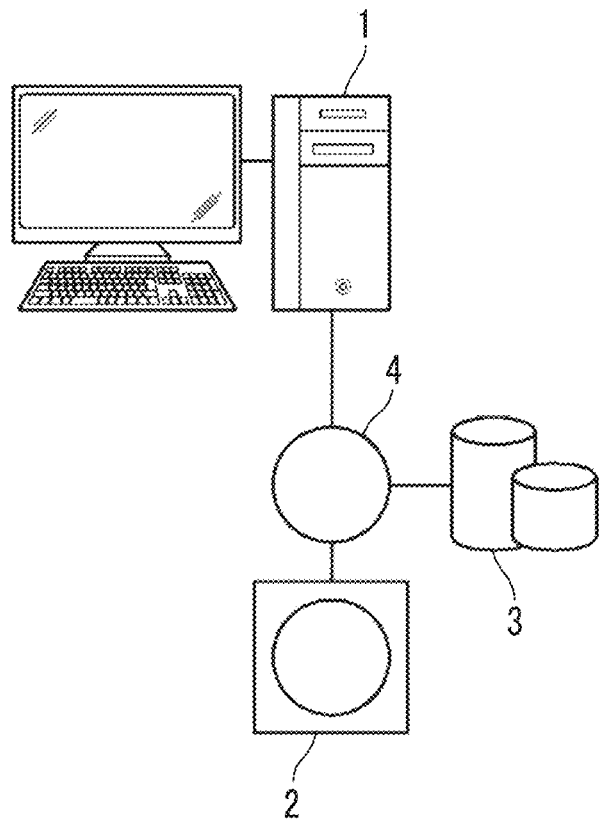
FIG. 1 is a hardware configuration diagram showing an outline of a diagnostic support system to which an image diagnosis support apparatus that is an embodiment of the disclosure is applied.
FIG. 2 is a diagram showing examples of an examination and a series.

Hereinafter, embodiments of the disclosure will be described with reference to the accompanying diagrams. FIG. 1 is a hardware configuration diagram showing the outline of a diagnostic support system to which an image diagnosis support apparatus according to an embodiment of the disclosure is applied. As shown in FIG. 1, in the diagnostic support system, an image diagnosis support apparatus 1 according to the present embodiment, a three-dimensional image capturing apparatus 2, and an image storage server 3 are communicably connected to each other through a network 4. The image storage server 3 corresponds to a data storage unit of the disclosure.

The three-dimensional image capturing apparatus 2 is an apparatus that generates a three-dimensional image showing a diagnostic target part of a subject by imaging the diagnostic target part. Specifically, the three-dimensional image capturing apparatus 2 is a CT apparatus, an MRI apparatus, a positron emission tomography (PET) apparatus, or the like. The three-dimensional image formed by a plurality of slice images, which is generated by the three-dimensional image capturing apparatus 2, is transmitted to the image storage server 3 and stored therein for each unit examination.

The image storage server 3 is a computer that stores and manages various kinds of data, and comprises a large-capacity external storage device and software for database management. The image storage server 3 communicates with other devices through the wired or wireless network 4 to transmit and receive image data or the like. Specifically, the image storage server 3 acquires various kinds of data including image data of the three-dimensional image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DICOM).

In the present embodiment, three-dimensional images of the subject and accessory images acquired in respective examinations performed at different times for the same subject are stored in the image storage server 3. FIG. 2 is a diagram showing examples of an examination and a series. As shown in FIG. 2, a plurality of series, such as series 1, series 2, series 3, . . . acquired in each unit examination using an abdominal CT and a head MRI, are stored in the image storage server 3. In the disclosure, "a plurality of series" corresponds to "a plurality of image data groups", and "a series" corresponds to "an image data group". The series is volume data acquired in one imaging, and the volume data is a three-dimensional image obtained by reconstructing a plurality of pieces of slice image data output from a tomographic apparatus, for example, a CT apparatus or an MRI apparatus.

For example, in a case where a head CT examination is performed as one examination, as shown in FIG. 2 as an example, it is assumed that volume data of a non-contrast CT acquired without administration of a contrast agent to the subject is series 1, arterial phase volume data acquired within a predetermined time by administering a contrast agent to the subject is series 2, and arterial phase volume data acquired after a time longer than the predetermined time passes from the administration of a contrast agent to the subject is series 3.

In addition, for example, in a case where a head MRI examination is performed as one examination, as shown in FIG. 2 as an example, it is assumed that volume data acquired by different imaging protocols, for example, volume data configured to include diffusion weighted images is series 1, volume data configured by an apparent diffusion coefficient (ADC) map is series 2, and volume data configured to include FLAIR images acquired using a fluid attenuation inversion recovery (FLAIR) method is series 3. The ADC map is an image in which the ADC is calculated for each pixel and arranged corresponding to the pixel position of the diffusion weighted image.

The accessory information includes, for example, an image identification (ID) for identifying each image, a patient ID for identifying a subject, an examination ID for identifying an examination, a unique ID (UID: unique identification) allocated for each medical image, examination date and examination time at which the medical image has been generated, the type of a modality used in an examination for acquiring the medical image, patient information such as patient's name, age, and gender, an examination part (imaging part), imaging conditions (such as the presence or absence of a contrast agent or a radiation dose), and information such as a series number in a case where a plurality of medical images are acquired in one examination.

The image diagnosis support apparatus 1 is realized by installing an image diagnosis support program of the disclosure on one computer. The computer may be a workstation or a personal computer that is directly operated by a doctor who performs diagnosis, or may be a server computer connected to these through a network. The image diagnosis support program is distributed in a state in which the image diagnosis support program is recorded on a recording medium, such as a digital versatile disc (DVD) or a compact disk read only memory (CD-ROM), and is installed onto the computer from the recording medium. Alternatively, the image diagnosis support program is stored in a storage device of a server computer connected to the network or in a network storage so as to be accessible from the outside, and is downloaded and installed onto a computer used by a doctor as necessary.

Figure 3:
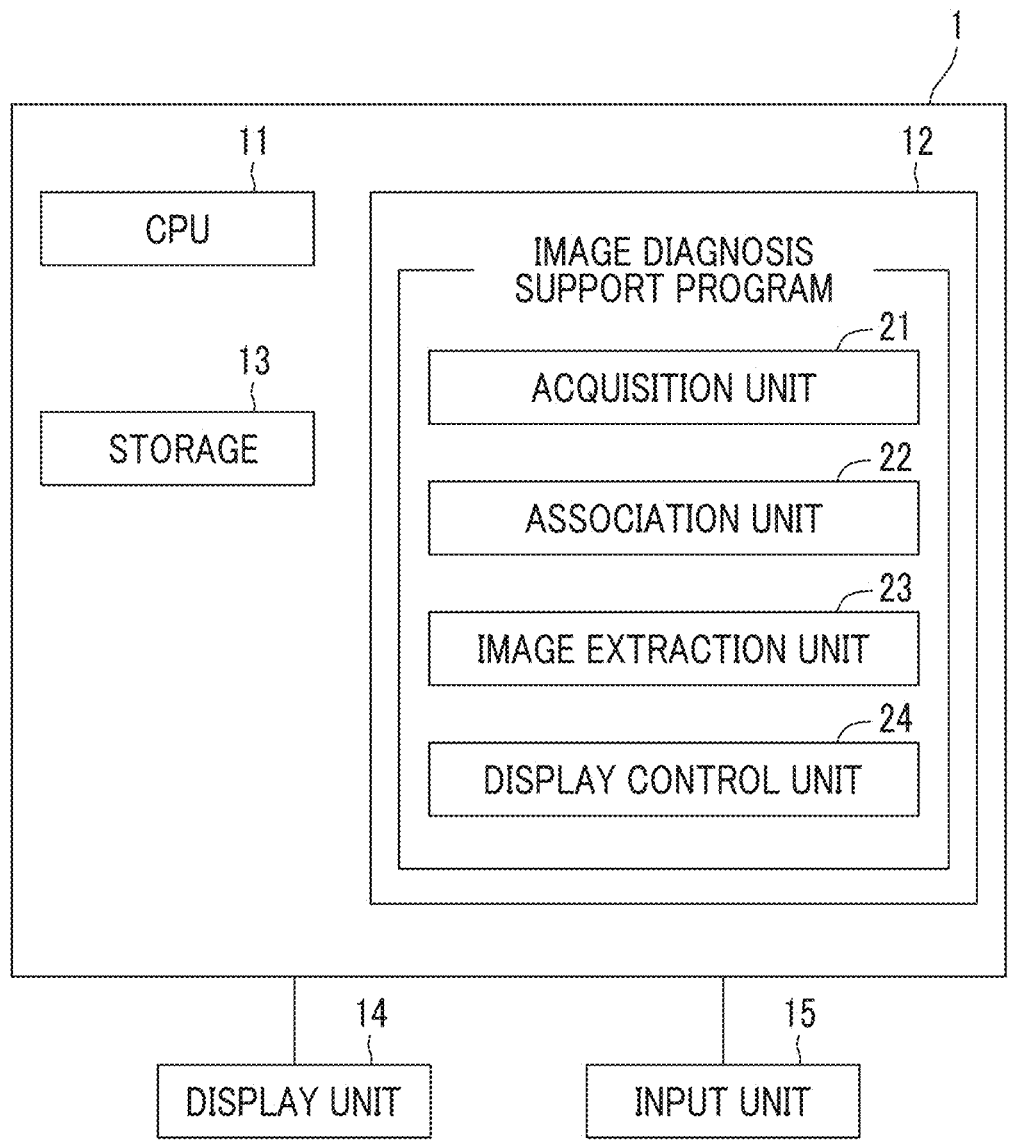
FIG. 3 is a schematic block diagram showing the configuration of the image diagnosis support apparatus that is an embodiment of the disclosure.

FIG. 3 is a diagram showing the schematic configuration of an image diagnosis support apparatus that is an embodiment of the disclosure realized by installing the image diagnosis support program onto a computer. As shown in FIG. 3, the image diagnosis support apparatus 1 comprises a central processing unit (CPU) 11, a memory 12, and a storage 13 as the configuration of a standard workstation. A display unit 14, such as a liquid crystal display, and an input unit 15, such as a keyboard and a mouse, are connected to the image diagnosis support apparatus 1. The display unit 14 displays sets of images to be subjected to comparative interpretation, which will be described later, in a contrastable layout. The input unit 15 receives various setting inputs from the user. For example, the input unit 15 receives a setting input of identification information of a patient and the selection of a target image to be described later. By using a touch panel, the display unit 14 and the input unit 15 may be used in common.

The storage 13 is a hard disk drive, a solid state drive (SSD), or the like. Examination images of the subject and various kinds of information including information necessary for processing, which are acquired from the image storage server 3 through the network 4, are stored in the storage 13.

An image diagnosis support program is stored in the memory 12. As processing to be executed by the CPU 11, the image diagnosis support program defines: acquisition processing for acquiring a plurality of first image data groups and a plurality of second image data groups to be subjected to comparative interpretation from a data storage unit (image storage server 3) in which a plurality of image data groups each including a plurality of images are stored for each unit examination; association processing for associating each image data group of the plurality of first image data groups with each image data group of the plurality of second image data groups based on the degree of similarity between each of the plurality of first image data groups and each of the plurality of second image data groups; image extraction processing for extracting a corresponding image corresponding to at least one target image of a first image data group from a second image data group, which is any image data group among the plurality of second image data groups associated with the first image data group, which is any image data group among the plurality of first image data groups; and display control processing for displaying sets of images of the target image and the corresponding image on a display unit in a contrastable layout.

Then, the CPU 11 executes these processes according to the program, so that the computer functions as an acquisition unit 21, an association unit 22, an image extraction unit 23, and a display controller 24.

The acquisition unit 21 reads and acquires, based on identification information of a patient input by the user using the input unit 15, a plurality of series acquired by imaging the same subject having the identification information at different imaging times from the image storage server 3. In a case where a plurality of series are already stored in the storage 13, the acquisition unit 21 may acquire the plurality of series from the storage 13.

The acquisition unit 21 acquires a plurality of series acquired by current examination as a current series Sc and a plurality of series acquired by examination before the current examination (hereinafter, referred to as past examination) as a past series Sp. Here, the current series Sc corresponds to the plurality of first image data groups of the disclosure, and the past series Sp corresponds to the plurality of second image data groups of the disclosure. Each series of the current series Sc and the past series Sp is configured to include a plurality of slice images captured by a CT apparatus or an MRI apparatus. It is assumed that the current series Sc and the past series Sp are images acquired by the three-dimensional image capturing apparatus 2 based on the same imaging principle. In addition, volume data including tomographic images, such as axial tomographic images, sagittal tomographic images, and coronal tomographic images, is acquired as a series.

Figure 4:
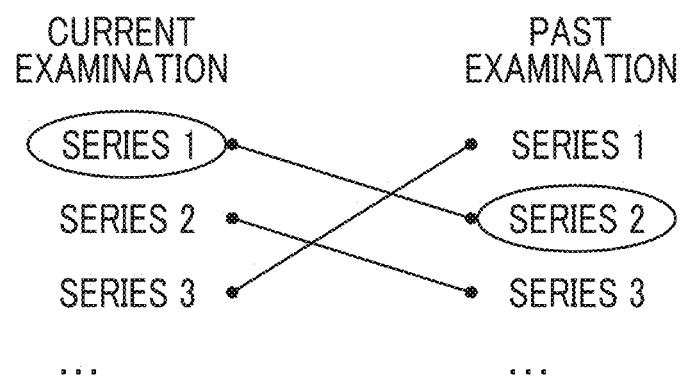
FIG. 4 is a diagram illustrating association between the series.

The association unit 22 associates each series of the current series Sc with each series of the past series Sp based on the degree of similarity between each series of the current series Sc and each series of the past series Sp. FIG. 4 is a diagram illustrating association between series.

As shown in FIG. 4, the association unit 22 associates each of a plurality of series including the series 1, the series 2, and the series 3 of the current series Sc acquired in the current examination with each of a plurality of series including the series 1, the series 2, and the series 3 of the past series Sp acquired in the past examination. In the case of associating the series, two or more series of the past series Sp are not associated with one series of the current series Sc. That is, it is assumed that one series of the past series Sp is associated with one series of the current series Sc.

Figure 5:
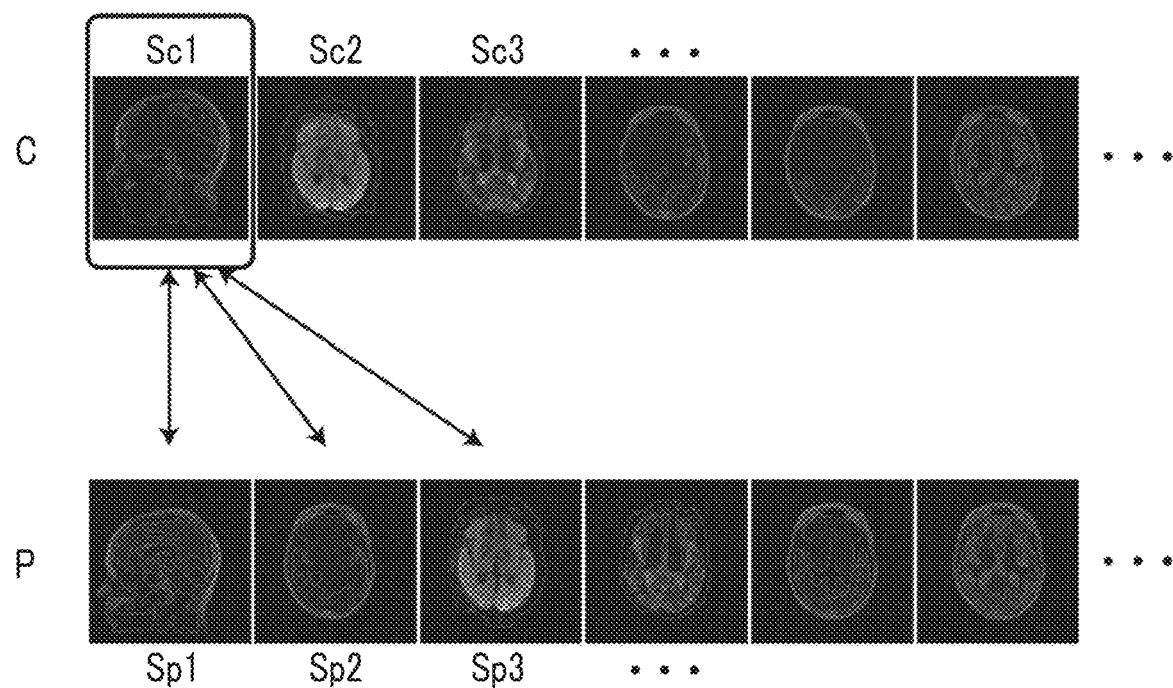
FIG. 5 is a diagram illustrating an embodiment of association between series (first example).
Figure 6:
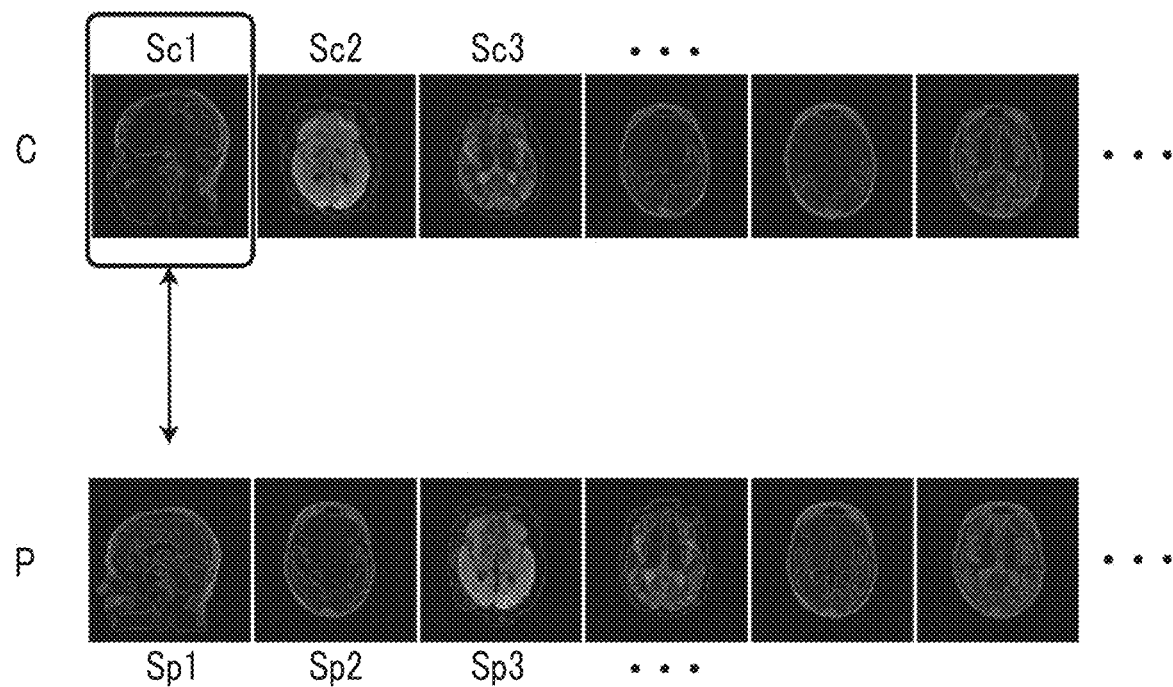
FIG. 6 is a diagram illustrating an embodiment of association between series (second example).
Figure 7:
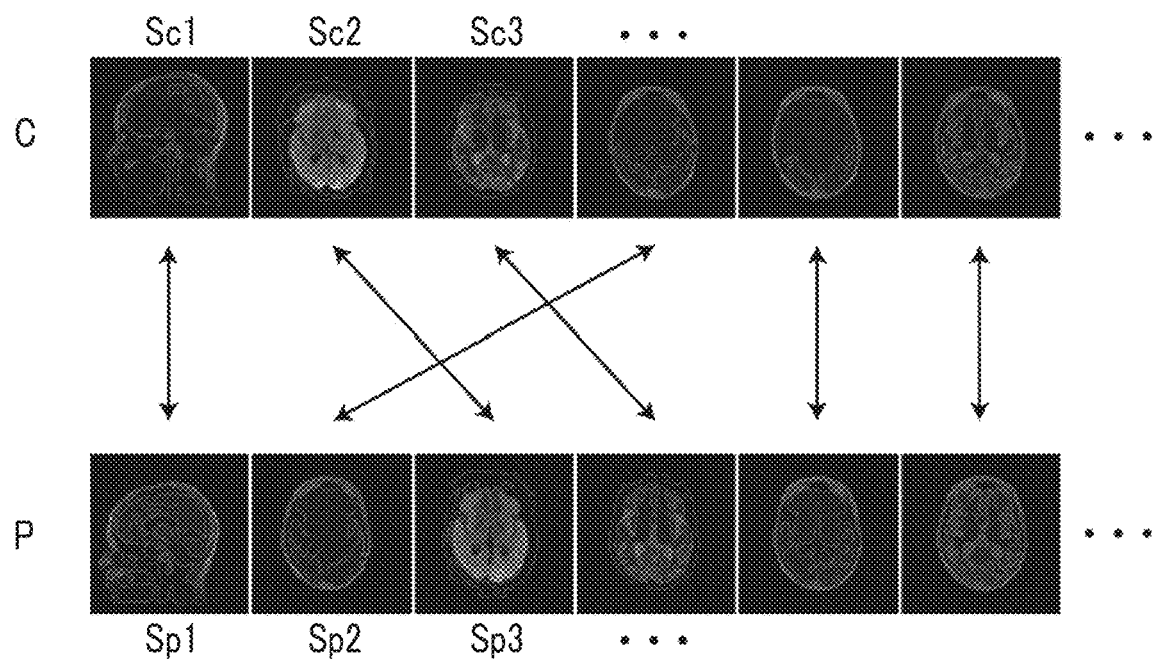
FIG. 7 is a diagram illustrating an embodiment of association between series (third example).

FIGS. 5, 6, and 7 are diagrams illustrating an embodiment of association between series. In FIGS. 5, 6, and 7, for the sake of convenience, each series is expressed as a two-dimensional image. In practice, however, each series is a three-dimensional image, that is, volume data. The association unit 22 calculates, for each series of the current series Sc acquired in the current examination C, the degree of similarity with each series of the past series Sp acquired in the past examination P, and associates the series having the highest degree of similarity between series. That is, as shown in FIG. 5 as an example, in a case where the current series Sc has a plurality of series Sc1, Sc2, Sc3, . . . and the past series Sp has a plurality of series Sp1, Sp2, Sp3, . . . , the association unit 22 calculates, for the series Sc1, the degree of similarity between series, such as the degree of similarity between the series Sc1 and the series Sp1, the degree of similarity between the series Sc1 and the series Sp2, and the degree of similarity between the series Sc1 and the series Sp3.

Then, the association unit 22 determines a series having the highest degree of similarity with the series Sc1 as a series to be associated with the series Sc1. That is, as shown in FIG. 6 as an example, in a case where the combination of the series Sc1 and the series Sp1 has the highest degree of similarity, the association unit 22 associates the series Sc1 with the series Sp1.

Similarly for the other series Sc2, Sc3, . . . , as shown in FIG. 7 as an example, the association unit 22 performs association processing to associate the series Sc1, Sc2, Sc3, . . . of the current series Sc with the series Sp1, Sp2, Sp3, . . . of the past series Sp. The method of calculating the degree of similarity in the association unit 22 will be described in detail later.

Figure 8:
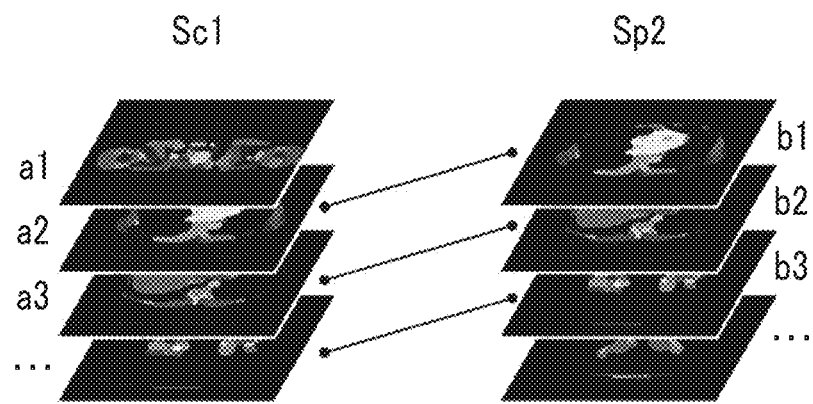
FIG. 8 is a diagram connecting associated images between a current series and a past series.

The image extraction unit 23 extracts a corresponding image corresponding to the target image of the current series Sc from the series of the past series Sp associated with the series in which the target image of the current series Sc is included. That is, a corresponding image corresponding to the target image of one series between the associated series is extracted from the other series. FIG. 8 is a diagram connecting associated images between the current series Sc1 and the past series Sp2. In the disclosure, as shown in FIG. 8, the image extraction unit 23 extracts a corresponding image, which corresponds to each of slice images a1, a2, a3, . . . forming the current series Sc1, from slice images b1, b2, b3, . . . forming the past series Sp2.

Between all the series associated by the association unit 22, the image extraction unit 23 extracts a slice image included in the past series Sp, which corresponds to each of all the slice images (hereinafter, referred to as target images) included in the current series Sc, as a corresponding image. In a case where the number of target images included in the series of the current series Sc is larger than the number of slice images included in the series of the past series Sp, one slice image is repeatedly extracted. That is, the image extraction unit 23 necessarily extracts one corresponding image for the corresponding image included in the series of the current series Sc.

Specifically, between all the series associated by the association unit 22, the image extraction unit 23 calculates a correlation value for all combinations of slice images, which are included in the past series Sp corresponding to each of all the target images included in the current series Sc, using the pixel value (for example, the CT value) of each slice image. Then, the image extraction unit 23 determines that the combination of slice images having the largest correlation value is a combination to be associated, and extracts a slice image of the past series Sp combined with the target image as a corresponding image. As a method of calculating a correlation value, for example, a correlation value may be calculated using zero-mean normalized cross-correlation (ZNCC). However, other calculation methods may be used without being limited thereto. For example, using the method of associating slice images described in JP2017-083403, a slice image of the past series Sp associated with the target image may be extracted as a corresponding image. Alternatively, a three-dimensional positional relationship may be determined using a known non-rigid registration technique, and slice images whose three-dimensional positional relationships match each other most may be associated with each other.

Figure 9:
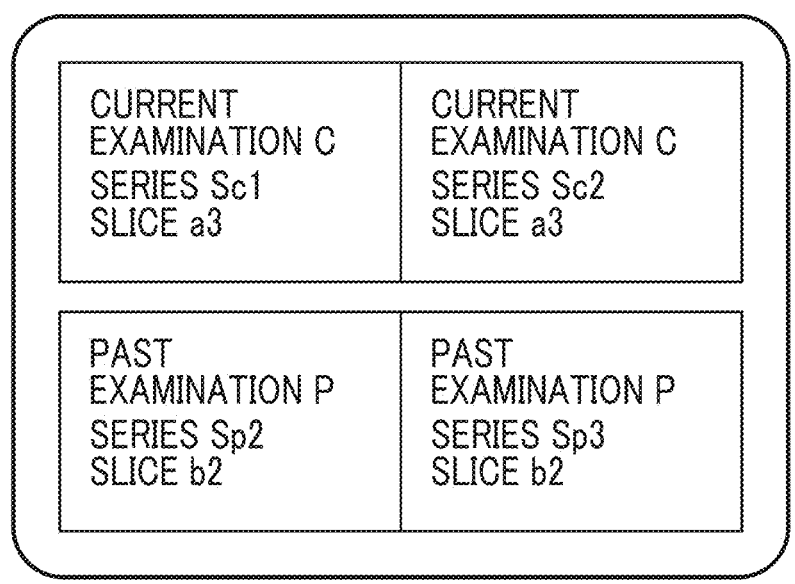
FIG. 9 is a diagram illustrating an example of the layout of a display unit.

The display controller 24 displays sets of images of each target image included in the current series Sc and a corresponding image included in the past series Sp, which corresponds to the target image, on the display unit in a contrastable layout. FIG. 9 is a diagram illustrating an example of the layout of the display unit 14. In addition, for the sake of convenience, the following description will be given with the upper side of the paper as an upper side in FIG. 9.

The display controller 24 displays sets of images of each target image included in the current series Sc and a corresponding image included in the past series Sp, which corresponds to the target image, in parallel on the screen of the display unit 14. Specifically, in a case where the series Sc1 of the current examination C and the series Sp2 of the past examination P are associated with each other and the series Sc2 of the current examination C and the series Sp3 of the past examination P are associated with each other by the association unit 22 and the corresponding image b2 of the series Sp2 is extracted for the target image a3 of the series Sc1 and the corresponding image b2 of the series Sp3 is extracted for the target image a3 of the series Sc2 by the image extraction unit 23, the display controller 24 displays sets of respective images in parallel vertically such that the images acquired in the current examination C are located on the upper side and the images acquired in the past examination P are located on the lower side, as a layout in which image sets of the target image a3 and the corresponding image b2 are contrastable, as shown in FIG. 9 as an example.

Figure 10:
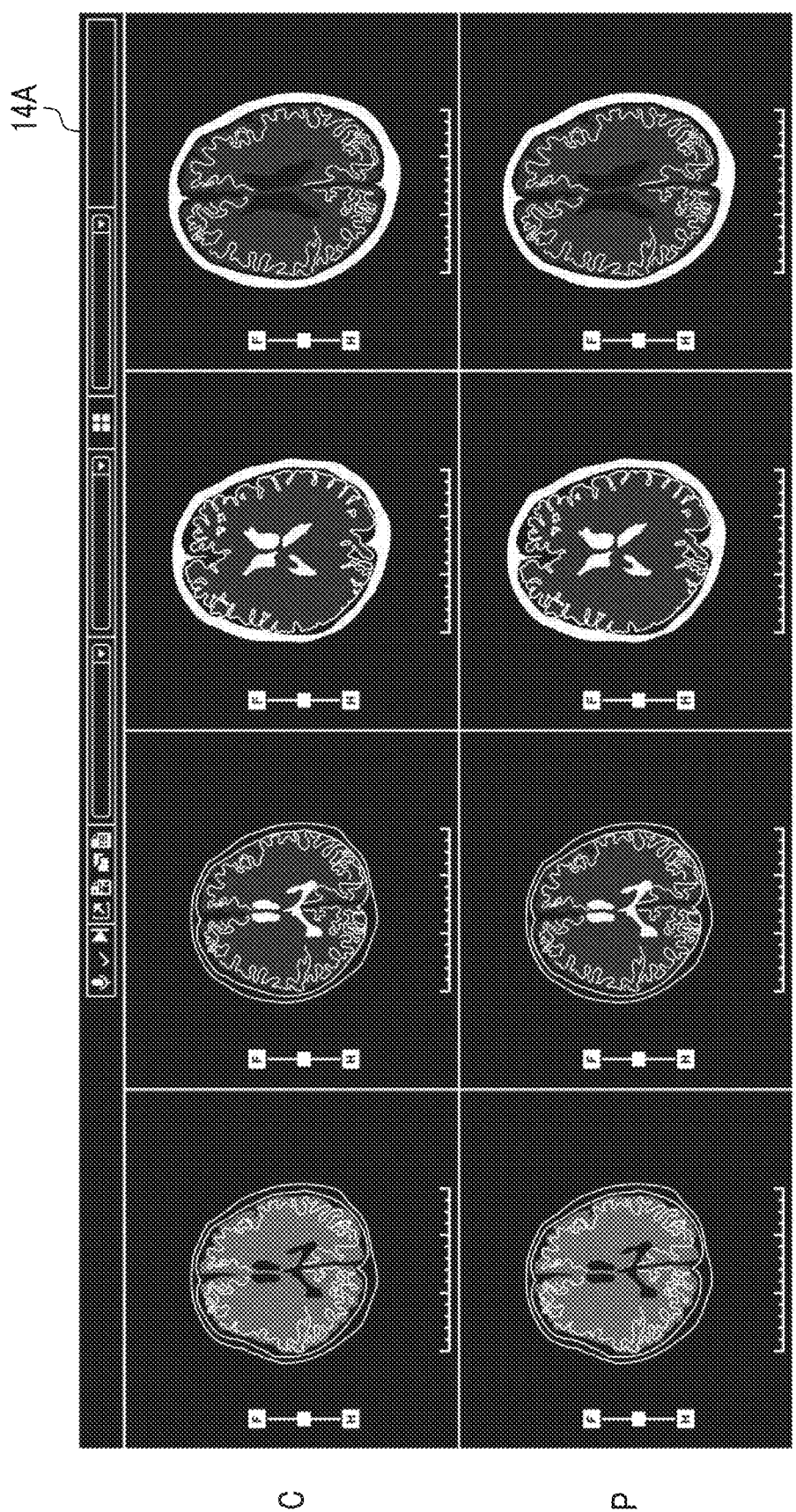
FIG. 10 is a diagram illustrating an example of a screen of a display unit.

FIG. 10 is a diagram illustrating an example of the screen of the display unit 14. In addition, for the sake of convenience, the following description will be given with the left side of the paper as an upper side in FIG. 10. As shown in FIG. 10 as an example, the display controller 24 displays each target image acquired in the current examination C and a corresponding image acquired in the past examination P corresponding to the target image in parallel vertically on a screen 14A of the display unit 14. The number of images that can be displayed on the screen 14A can be appropriately changed by the user. In addition, target images to be displayed on the upper side of the screen 14A can be appropriately selected and disposed by the user operating the input unit 15. The display controller 24 displays corresponding images, which correspond to the target images disposed by the user, in parallel below the target images.

Alternatively, the display controller 24 may display sets of images of all the corresponding images and the target images on the display unit 14. In a case where the number of target images is large, the user may display the sets of images, for example, by operating the input unit 15 to simultaneously scroll the sets of the target images and the corresponding images in the left and right direction.

In the technique of the disclosure, the display controller 24 is not limited to displaying the corresponding images and the target images in parallel vertically. For example, the corresponding images and the target images may be displayed in parallel horizontally.

Figure 11:
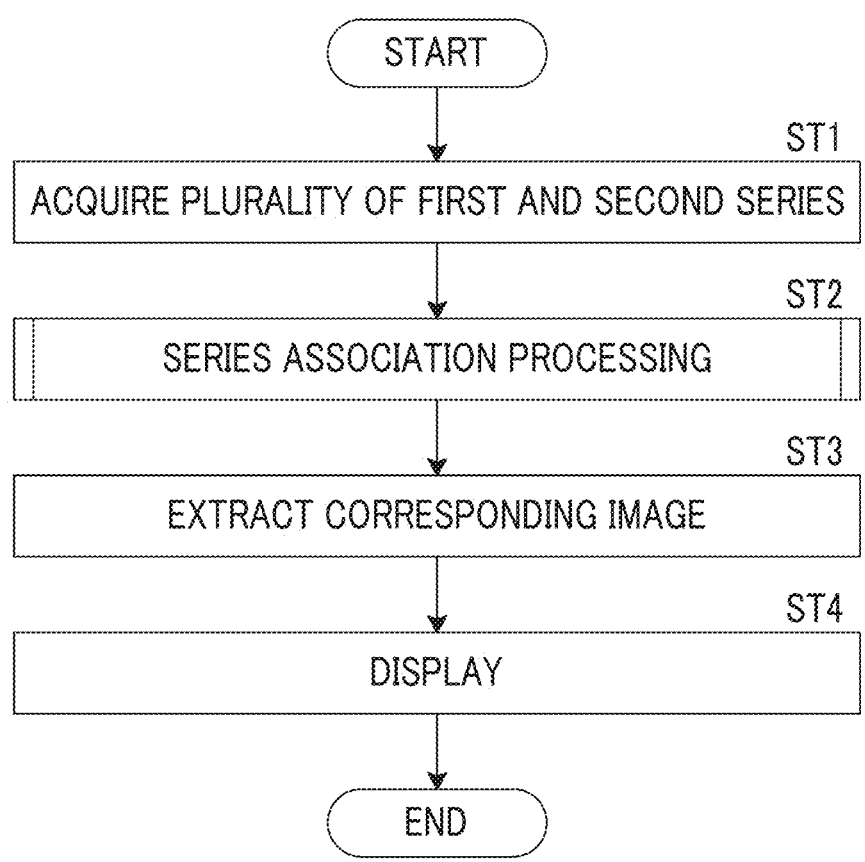
FIG. 11 is a flowchart showing a process performed in an embodiment of the disclosure.

Next, a process performed in the present embodiment will be described. FIG. 11 is a flowchart showing a process performed in an embodiment of the disclosure.

First, the acquisition unit 21 acquires a plurality of first series and a plurality of second series, which are acquired by imaging the patient at different imaging times, based on the input of identification information or the like of the patient by the user (step ST1). In the disclosure, the current series Sc and the past series Sp are acquired as a plurality of first series and a plurality of second series, respectively.

Next, the association unit 22 performs association processing of series to be associated based on the degree of similarity between each series of the current series Sc and each series of the past series Sp acquired by the acquisition unit 21 (step ST2).

Here, the series association processing by the association unit 22 will be described. The association unit 22 calculates the degree of similarity between pieces of pixel data used in the association between the series described above. Specifically, the degree of similarity can be acquired using a known technique, such as cross correlation or histogram intersection. However, it may be difficult to calculate an accurate degree of similarity with pixel data alone. For example, even between series of different image plane directions, such as axial and sagittal cross sections, the degree of similarity between pieces of pixel data may be high. Therefore, in the disclosure, the degree of similarity is calculated by further considering DICOM tag information relevant to the type of series or imaging information. Specifically, the direction of the image plane is determined with reference to accessory information, such as a DICOM tag, and the degree of similarity is calculated to be higher in a case where the directions of the image planes match each other and lower in a case where the directions of the image planes do not match each other.

In the disclosure, as an example, a method of calculating the degree of similarity between pieces of pixel data after determining the direction of each image plane with reference to "Image Orientation" included in the DICOM tag information is used. Here, "Image Orientation" defines the directions of "first row" and "first column" of the image with the subject as a reference. The direction of the image plane is determined based on "Image Orientation". "Image Orientation" can be defined based on the description of http://dicom.nema.org/medical/dicom/current/output/chtml/part03/sect_C.7.6.2.html#sect_C0.7.6.2.1.1 (search date: Aug. 23, 2018). For example, in a case where the image is an axial cross section perpendicular to the body axis of the subject, "first row" of "Image Orientation" almost matches (1, 0, 0) and "first column" thereof almost matches (0, 1, 0). Therefore, the direction of the image plane in the image can be determined by calculating the degree of matching between two vectors obtained by referring to "Image Orientation" and (1, 0, 0) and (0, 1, 0) using an inner product operation.

Figure 12:
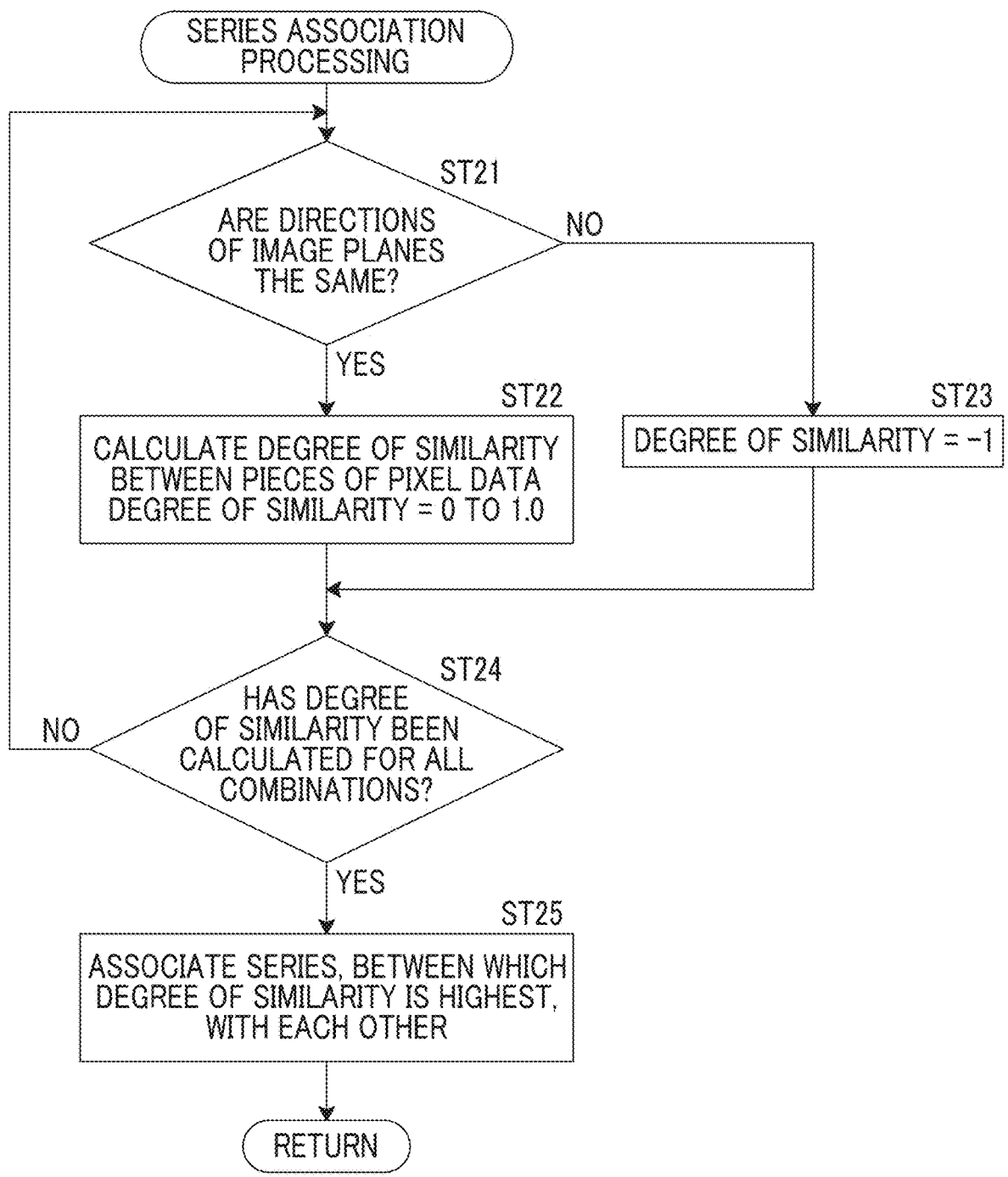
FIG. 12 is a flowchart showing a series association process performed in an embodiment of the disclosure.
Figure 13:
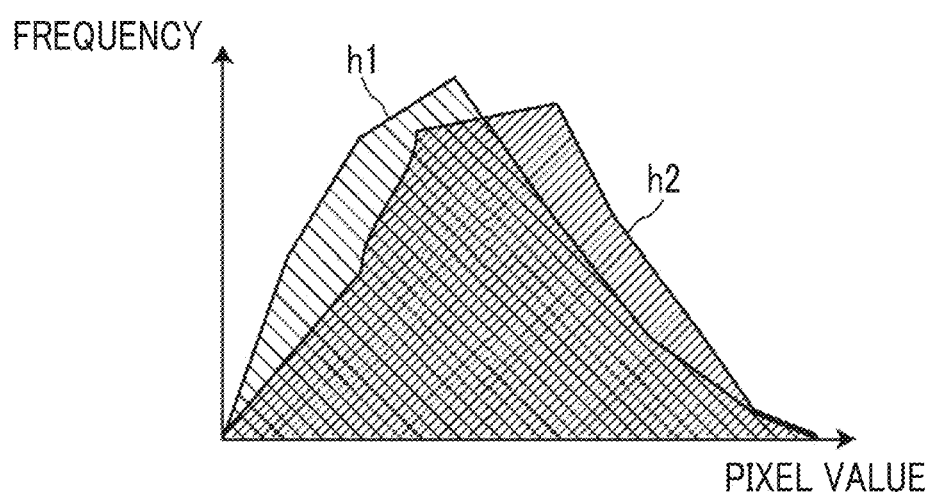
FIG. 13 is a diagram illustrating a method of calculating the degree of similarity from histogram intersection.

FIG. 12 is a flowchart showing a series association process performed in an embodiment of the disclosure, and FIG. 13 is a diagram illustrating a method of calculating the degree of similarity from the histogram intersection.

As shown in FIG. 12 as an example, first, the association unit 22 determines whether or not the direction of the image plane in the series Sc1 of the current series Sc is the same as that in the series Sp1 of the past series Sp (step ST21). The directions of the image planes of the series Sc1 and the series Sp1 can be determined based on the description of "Image Orientation" of the DICOM tag as described above. In a case where the directions of the image planes of the series Sc1 and the series Sp1 match each other (step ST21; Yes), the degree of similarity between pieces of pixel data is calculated (step ST22).

FIG. 13 is a diagram illustrating a method of calculating the degree of similarity from the histogram intersection. As shown in FIG. 13, the histogram intersection refers to the proportion of a common portion between a histogram h1 of the series Sc1 and a histogram h2 of the series Sp1. The degree of similarity is derived from the proportion of the common portion. Specifically, the degree of similarity is 1 in a case where the proportion of the common portion is 100%, and the degree of similarity is 0 in a case where the proportion of the common portion is 0%. Thus, the association unit 22 can calculate the degree of similarity of the entire volume data by using the series Sc1 and the series Sp1, that is, the pixel data of the entire volume data. The degree of similarity calculated herein is a value of 0 or more and 1.0 or less.

In order to reflect the rough composition of the series Sc1 and the series Sp1, for example, the vertical direction, the horizontal direction, and the height direction of each of the series Sc1 and the series Sp1 may be equally divided into three parts, a histogram intersection may be calculated in each of 3×3×3 sections, that is, each of 27 sections obtained by division, and the average value may be set as the degree of similarity between the series Sc1 and the series Sp1. The number of divisions is not limited to 27 sections, and can be appropriately changed based on the required accuracy of association.

On the other hand, in a case where the directions of the image planes of the series Sc1 and the series Sp1 are not the same in step ST21 (step ST21; No), the association unit 22 sets the degree of similarity between pieces of pixel data to −1 (step ST23).

Then, the association unit 22 determines whether or not the degree of similarity has been calculated for all the combinations of the series of the current series Sc and the past series Sp (step ST24). In a case where the association unit 22 determines that the degree of similarity has been calculated for all the combinations (step ST24; YES), the association unit 22 associates a series in the current series Sc and a series in the past series Sp, between which the degree of similarity is the highest, with each other (step ST25).

On the other hand, in a case where the association unit 22 determines that the degree of similarity has not been calculated for all the combinations in step ST24 (step ST24; NO), the association unit 22 proceeds to step ST21, and repeats proceeding to step ST21 until the degree of similarity is calculated for all the combinations of series of the current series Sc and the past series Sp.

After the series association by the association unit 22 is ended as described above, the process returns to FIG. 11, and the image extraction unit 23 performs corresponding image extraction processing for extracting one corresponding image from slice images included in the series of the past series Sp associated in step ST2 for corresponding images included in each series of the current series Sc as described above (step ST3).

Then, as shown in FIG. 10 as an example, the display controller 24 displays each target image acquired in the current examination C and a corresponding image acquired in the past examination P corresponding to the target image in parallel vertically on the screen 14A of the display unit 14 as described above (step ST4), and the series of processes are ended.

Thus, according to the above embodiment of the disclosure, the current series Sc and the past series Sp to be subjected to comparative interpretation are acquired from the image storage server 3, each series of the current series Sc and each series of the past series Sp are associated with each other based on the degree of similarity between each series of the current series Sc and each series of the past series Sp, a corresponding image corresponding to at least one target image of the series Sc1 is extracted from the series Sp2 that is any series of the past series Sp associated with the series Sc1 that is any series of the current series Sc, and sets of images of the target image and the corresponding image are displayed on the display unit in a contrastable layout. Therefore, it is possible to appropriately associate sets of series to be subjected to comparative interpretation and to extract corresponding slice images between the associated sets of series and display the extracted corresponding slice images in a contrastable layout. In this manner, a slice image of the past examination corresponding to a slice image of the current examination can be displayed such that the slice image of the past examination automatically follows the slice image of the current examination. Therefore, in the case of comparing the current examination with the past examination, it is possible to reduce the time and effort required for the user to select a series or a slice image so as to be easily interpreted.

In the embodiment described above, in the calculation of the degree of similarity between pieces of volume data of series used at the time of series association as an example, the association unit 22 determines whether or not the directions of the image planes are the same in step ST21 shown in FIG. 12. However, the technique of the disclosure is not limited thereto. For example, in a case where information regarding the direction of the image plane is not present in the accessory information, such as a DICOM tag, the processing of step ST21 and step ST23 may be omitted and the degree of similarity may be calculated using only pixel data.

The method of association between the series by the association unit 22 is not limited to the above embodiment, and an association method described in JP2018-074188 can be used.

In the embodiment described above, as an example, the image extraction unit 23 extracts a slice image included in the past series Sp that corresponds to each of all the target images included in the current series Sc, as a corresponding image, between all the series associated by the association unit 22. However, the method of the disclosure is not limited thereto. For example, in a case where it is set in advance in the image diagnosis support apparatus 1 that the image acquired in the current examination C disposed on the upper side of the screen 14A shown in FIG. 10 is only the series Sc1 of the current series Sc, the image extraction unit 23 may extract a corresponding image only for the target image included in the series Sc1.

Figure 14:
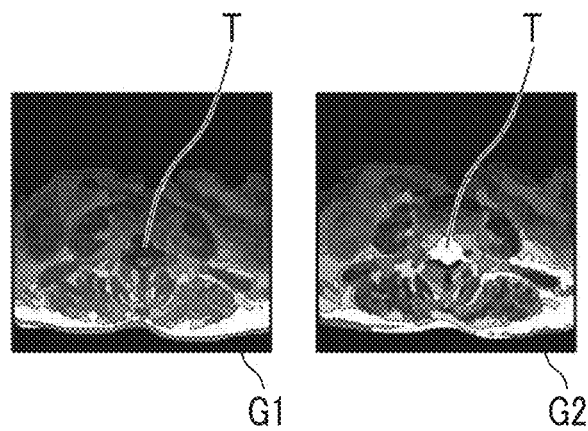
FIG. 14 is a diagram illustrating a method of detecting a region including a specific anatomical structure and performing association between the series (first example).
Figure 15:
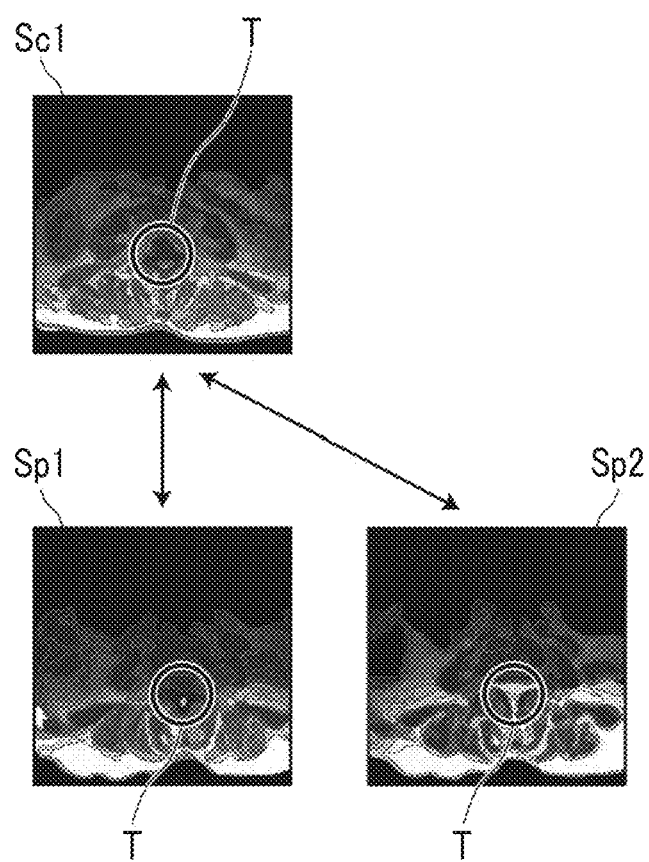
FIG. 15 is a diagram illustrating a method of detecting a region including a specific anatomical structure and performing association between the series (second example).

In the embodiment described above, as an example, the association unit 22 calculates the degree of similarity between the pieces of volume data of series in the case of associating the series. However, the method of the disclosure is not limited thereto. The association unit 22 may calculate the degree of similarity by detecting a region including a specific anatomical structure from each series included in the current series Sc and the past series Sp and comparing the pixel value distributions as feature amounts of the detected regions. FIGS. 14 and 15 are diagrams illustrating a method of detecting a region including a specific anatomical structure and performing association between the series.

In general, a T1-weighted image is an image of a nuclear magnetization distribution mainly contrasted by longitudinal relaxation, and a T2-weighted image is an image of a nuclear magnetization distribution mainly contrasted by lateral relaxation. In the T2-weighted image, water, blood, fat, and the like become high signals (white), and bleeding, calcification, fibrous tissue, melanin, and the like become low signals (black).

Therefore, as shown in FIG. 14 as an example, the association unit 22 detects a region including the spinal cord from each series, that is, each piece of volume data, and compares the pixel value distributions, that is, histograms of the detected regions including the spinal cord. As shown in FIG. 14, in a T2-weighted image G2, a spinal cord region T shows a high signal, but in a T1-weighted image G1, the spinal cord region T does not show a high signal. Therefore, the T2-weighted image G2 can be distinguished from other images, such as the T1-weighted image G1, by comparing the histograms of the detected regions including the spinal cord.

Specifically, as shown in FIG. 15, the association unit 22 determines association between the series by performing histogram comparison between a region including the spinal cord of the series Sc1 of the current series Sc and each region including the spinal cord of all the series included in the past series Sp. Regions between which histogram comparison is to be performed are not limited to the regions including the spinal cord, and may be regions including a specific anatomical structure. The specific anatomical structure is determined based on the type of the subject imaged by the current examination C and the past examination P. In this manner, it is possible to determine the association between the series by comparing the histograms of regions including a specific anatomical structure.

Figure 16:
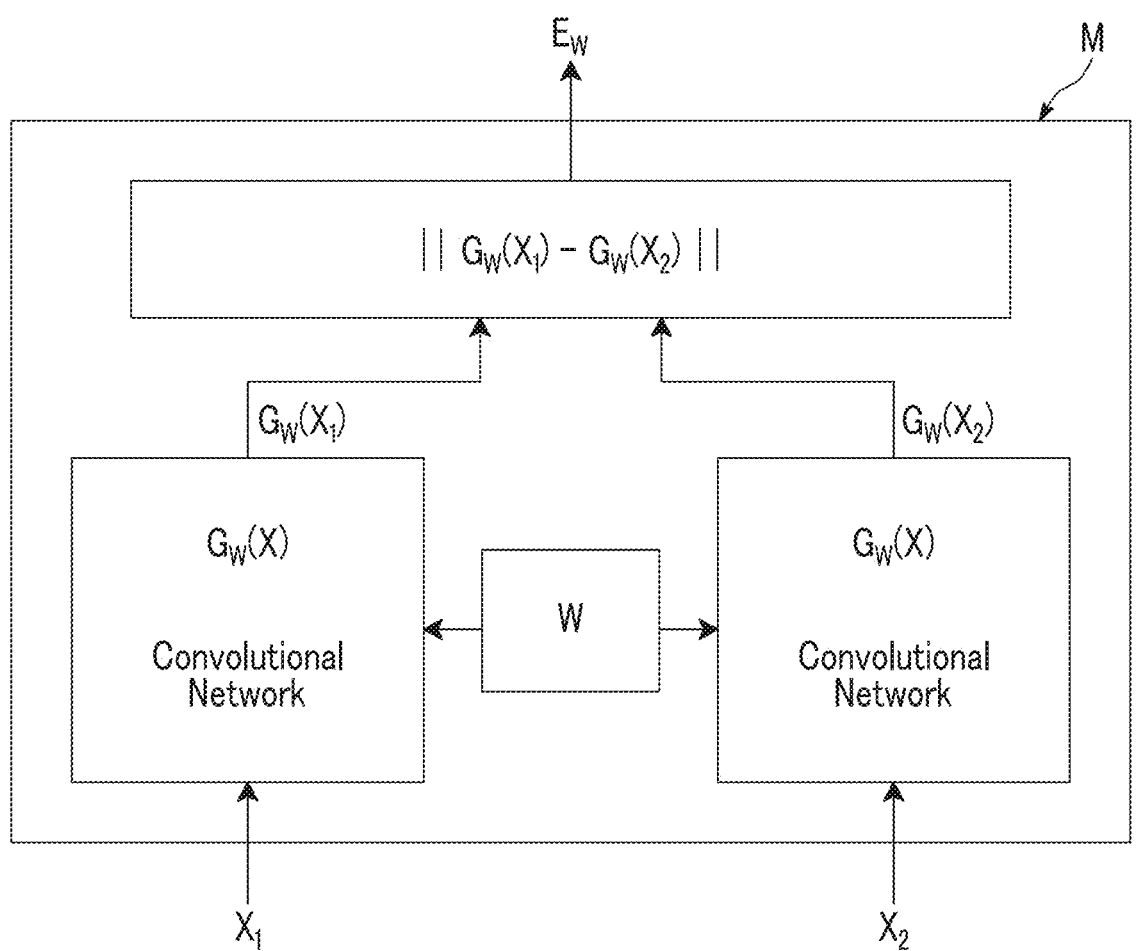
FIG. 16 is a diagram illustrating a learned model.
Figure 17:
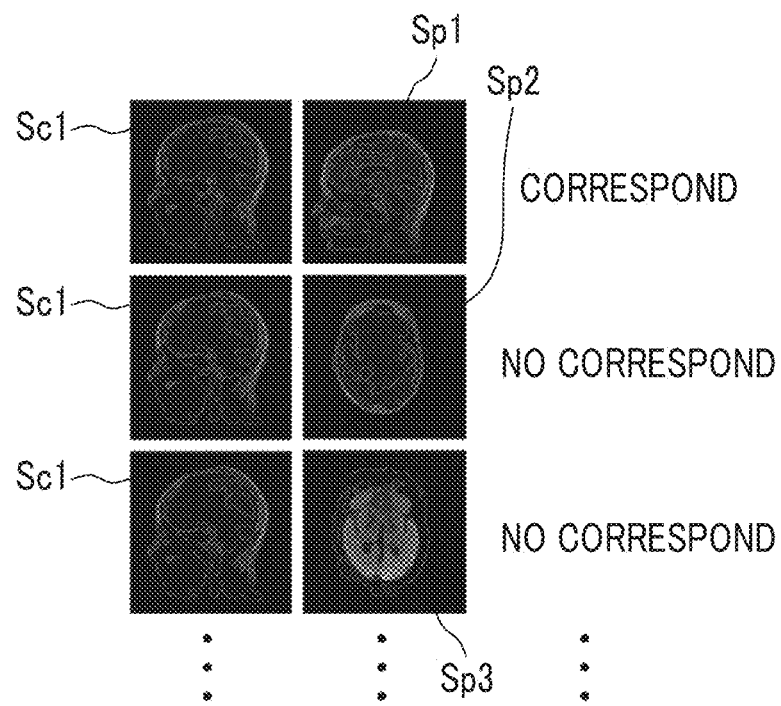
FIG. 17 is a diagram illustrating correct answer data of association between series.

In addition, the association unit 22 may have a learned model on which machine learning has been performed so as to output the series of the past series Sp having a highest degree of similarity with an input series based on the input of each series of the current series Sc. By preparing a number of correct answer data of the association between the series, it is possible to combine the series association methods described above with reference to FIGS. 12 to 15 with the machine learning. In the disclosure, as a learned model M, a Siamese Network is used, for example. FIG. 16 is a diagram illustrating a learned model, and FIG. 17 is a diagram illustrating correct answer data of association between series.

As the learned model M, for example, a Siamese Network that is a network having a structure shown in FIG. 16 is used. The Siamese Network can be learned so that the distance between Convolutional Network outputs Gw(X1) and Gw(X2) for two inputs X1 and X2 is short in a case where the two inputs X1 and X2 need to be associated with each other and long in a case where the two inputs X1 and X2 do not need to be associated with each other. Specifically, the technique described in S. Chopra, R. Hadsell, Y. LeCun, "Learning a Similarity Metric Discriminatively, with Application to Face Verification", International Conference on Computer Vision and Pattern Recognition (CVPR), 2005. can be used.

For example, in a case where the association between the series shown in FIG. 7 is the correct answer of association, the correct answer data for learning has two series as its input and "correspond" or "no correspond" as its output. As shown in FIG. 17, "correspond" is the output in a case where the series Sc1 and the series Sp1 are the input, "no correspond" is the output in a case where the series Sc1 and the series Sp2 are the input, and "no correspond" is the output in a case where the series Sc1 and the series Sp3 are the input. The inputs X1 and X2 may be histograms of the entire series (volume), or may be histograms of regions including a specific anatomical structure, or may be pixel data itself. As described above, the association unit 22 can perform association between the series using the learned model M.

In the technique of the disclosure, the learned model is not limited to one using the Siamese Network. The learned model M may use, for example, Triplet Network having a total of three series of one target series, a series corresponding to the target series, and a series not corresponding to the target series, as its input. For the Triplet Network, it is possible to use the technique described in Elad Hoffer, Nir Ailon, "DEEP METRIC LEARNING USING TRIPLET NETWORK", Accepted as a workshop contribution at ICLR (International Conference on Learning Representations) 2015.

Figure 18:
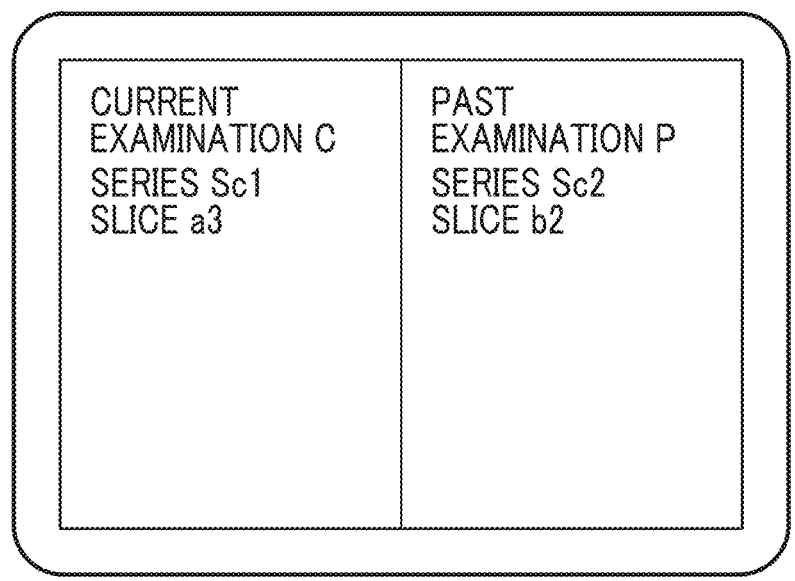
FIG. 18 is a diagram illustrating an example of the layout of a display unit.

In the embodiment described above, the display controller 24 displays the sets of images of the target image and the corresponding image in parallel on the screen 14A of the display unit 14. However, the display controller 24 of the disclosure is not limited thereto. The display controller 24 may display the sets of all images of the target image and the corresponding image on the screen 14B of the display unit 14 so as to be switched one by one. FIG. 18 is a diagram illustrating an example of the layout of the display unit 14. In addition, for the sake of convenience, the following description will be given with the upper side of the paper as an upper side in FIG. 18.

The display controller 24 displays sets of images of each target image included in the current series Sc and a corresponding image included in the past series Sp, which corresponds to the target image, on the screen 14B of the display unit 14 so as to be switched one by one. Specifically, as an example, in a case where the series Sc1 of the current examination C and the series Sp2 of the past examination P are associated with each other by the association unit 22 and the corresponding image b2 of the series Sp2 is extracted for the target image a3 of the series Sc1 by the image extraction unit 23, the display controller 24 displays sets of respective images in parallel horizontally such that the images acquired in the current examination C are located on the left side and the images acquired in the past examination P are located on the right side, as a layout in which image sets of the target image a3 and the corresponding image b2 are contrastable, as shown in FIG. 18 as an example.

Figure 19:
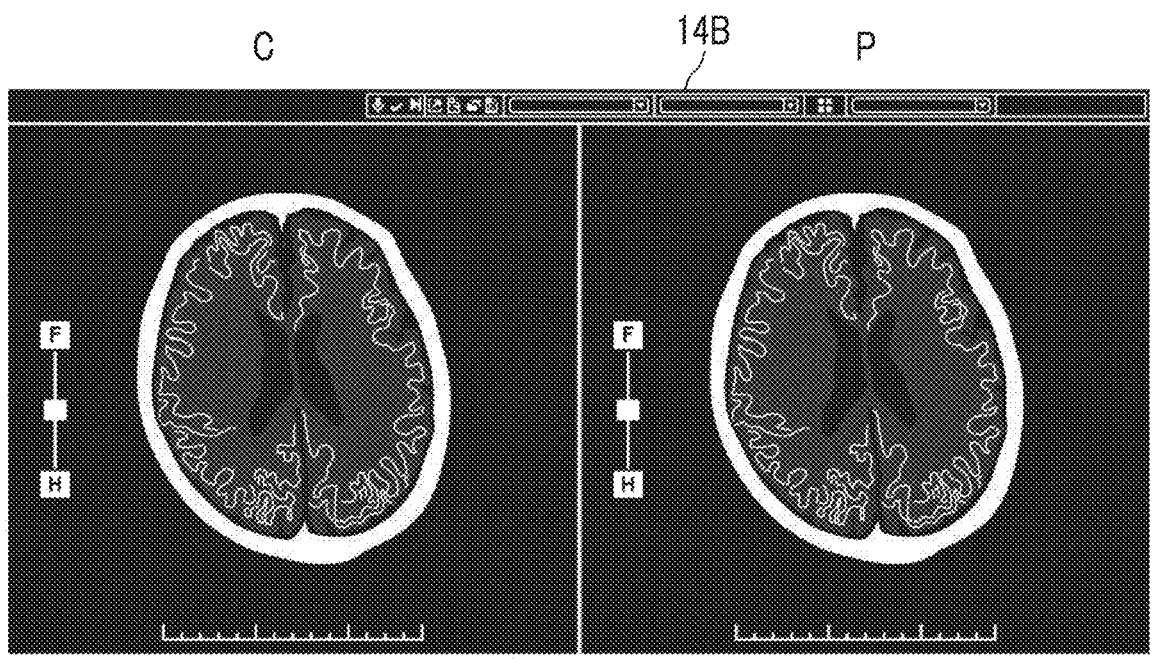
FIG. 19 is a diagram illustrating an example of the screen of a display unit.

FIG. 19 is a diagram illustrating an example of a screen 14B of the display unit 14. In addition, for the sake of convenience, the following description will be given with the upper side of the paper as an upper side in FIG. 19. As shown in FIG. 19 as an example, the display controller 24 displays one target image acquired in the current examination C and a corresponding image acquired in the past examination P corresponding to the target image in parallel horizontally on the screen 14B of the display unit 14. For example, each time the user operates the input unit 15, the display controller 24 displays the sets of images displayed on the screen 14B so as to be switched. The display controller 24 displays the sets of images of all the corresponding images and the target images on the display unit 14 so as to be sequentially switched.

The target images sequentially displayed on the screen 14B can be appropriately changed by the user. That is, all the target images may be used, or only the target image selected in advance by the user may be used. In any case, corresponding images extracted by the image extraction unit 23 for the sequentially displayed target images are displayed on the screen 14B together with the target images.

For example, the display controller 24 of the disclosure may display the screen 14B shown in FIG. 19 in a case where the user selects a full image display function, a full screen display function, and the like by operating the input unit 15 and display the screen 14A shown in FIG. 10 in a case where the selection of the full image display function, the full screen display function, and the like is canceled.

In the above embodiment, each series has been described as a three-dimensional image as an example. However, the technique of the disclosure is not limited thereto. For example, a plurality of two-dimensional images continuously captured and a four-dimensional image can be a series. Here, the four-dimensional image means a three-dimensional motion picture of the heart.

In the above embodiment, the "plurality of first image data groups" and the "plurality of second image data groups" of the disclosure are the current series Sc and the past series Sp that are acquired by capturing the same subject at different times. However, the technique of the disclosure is not limited thereto. For example, the "plurality of first image data groups" may be the current series Sc, and the plurality of second image data groups" may be a series including a plurality of images of the atlas, which is a map created by continuously combining cross-sectional images along various anatomical planes of the subject, or the plurality of second image data groups" may be a plurality of series acquired by imaging a subject different from the subject for the "plurality of first image data groups".

In the embodiment described above, for example, various processors shown below can be used as the hardware structures of processing units for executing various kinds of processing, such as the acquisition unit 21, the association unit 22, the image extraction unit 23, and the display controller 24. The various processors include not only the above-described CPU, which is a general-purpose processor that executes software (program) to function as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, as the hardware structure of these various processors, it is possible to use an electrical circuit (circuitry) in which circuit elements, such as semiconductor elements, are combined.

What is claimed is:

1. An image diagnosis support apparatus, comprising:
a memory; and
a processor configured to:
acquire a plurality of first image data groups and a plurality of second image data groups to be subjected to comparative interpretation from a data storage unit in which multiple image data groups each including a plurality of images are stored for each unit examination;
associate each image data group of the plurality of first image data groups with each image data group of the plurality of second image data groups based on a degree of similarity between pieces of pixel data of each of the plurality of first image data groups and pieces of pixel data of each of the plurality of second image data groups acquired by the processor;
extract a corresponding image corresponding to at least one target image of a first image data group from a second image data group, which is any image data group among the plurality of second image data groups associated with the first image data group, which is any image data group among the plurality of first image data groups;
display a set of images of the target image and the corresponding image on a display unit in a contrastable layout;
determine whether or not a direction of image planes in the plurality of first image data groups is the same as a direction of image planes in the plurality of second image data groups; and
in a case in which the directions of the image planes of the plurality of first image data groups and the plurality of second image data groups match each other, calculate the degree of similarity.

2. The image diagnosis support apparatus according to claim 1,
wherein the processor is further configured to extract the corresponding image for all target images included in the plurality of first image data groups.

3. The image diagnosis support apparatus according to claim 2,
wherein the processor is further configured to display sets of images of all of the target images and the corresponding images.

4. The image diagnosis support apparatus according to claim 2,
wherein the processor is further configured to display sets of the target images and the corresponding images in parallel on a screen of the display unit.

5. The image diagnosis support apparatus according to claim 2,
wherein the image data groups are volume data configured to include a plurality of slice images, and the processor is further configured to perform association based on the degree of similarity.

6. The image diagnosis support apparatus according to claim 2,
wherein the processor is further configured to process a learned model on which machine learning has been performed so as to output whether or not combinations of input image data groups based on input of any involved image data group among the plurality of first image data groups and any involved image data group among the plurality of second image data groups correspond to each other.

7. The image diagnosis support apparatus according to claim 3,
wherein the processor is further configured to display the sets of all of the target images and the corresponding images on a screen of the display unit so as to be switched one by one.

8. The image diagnosis support apparatus according to claim 4,
wherein the image data groups are volume data configured to include a plurality of slice images, and the processor is further configured to perform association based on the degree of similarity.

9. The image diagnosis support apparatus according to claim 4,
wherein the processor is further configured to perform association based on a feature amount in a region including a specific anatomical structure included in each involved image data group.

10. The image diagnosis support apparatus according to claim 4,
wherein the processor is further configured to process a learned model on which machine learning has been performed so as to output whether or not combinations of input image data groups based on input of any involved image data group among the plurality of first image data groups and any involved image data group among the plurality of second image data groups correspond to each other.

11. The image diagnosis support apparatus according to claim 7,
wherein the image data groups are volume data configured to include a plurality of slice images, and the processor is further configured to perform association based on the degree of similarity.

12. The image diagnosis support apparatus according to claim 7,
wherein the processor is further configured to perform association based on a feature amount in a region including a specific anatomical structure included in each involved image data group.

13. The image diagnosis support apparatus according to claim 7,
wherein the processor is further configured to process a learned model on which machine learning has been performed so as to output whether or not combinations of input image data groups based on input of any involved image data group among the plurality of first image data groups and any involved image data group among the plurality of second image data groups correspond to each other.

14. The image diagnosis support apparatus according to claim 1,
wherein the image data groups are volume data configured to include a plurality of slice images, and the processor is further configured to perform association based on the degree of similarity.

15. The image diagnosis support apparatus according to claim 1,
wherein the processor is further configured to perform association based on a feature amount in a region including a specific anatomical structure included in each involved image data group.

16. The image diagnosis support apparatus according to claim 1,
wherein the processor is further configured to process a learned model on which machine learning has been performed so as to output whether or not combinations of input image data groups based on input of any involved image data group among the plurality of first image data groups and any involved image data group among the plurality of second image data groups correspond to each other.

17. The image diagnosis support apparatus according to claim 1,
wherein the processor is further configured to extract the corresponding image based on the degree of similarity, the degree of similarity being a degree of similarity between the target image and each image of the second image data group.

18. The image diagnosis support apparatus according to claim 1,
wherein the plurality of first image data groups and the plurality of second image data groups are acquired by imaging the same subject at different imaging times.

19. An image diagnosis support method, comprising:
acquiring a plurality of first image data groups and a plurality of second image data groups to be subjected to comparative interpretation from a data storage unit in which multiple image data groups each including a plurality of images are stored for each unit examination;
associating each image data group of the plurality of first image data groups with each image data group of the plurality of second image data groups based on a degree of similarity between pieces of pixel data of each of the plurality of first image data groups and pieces of pixel data of each of the plurality of second image data groups;
extracting a corresponding image corresponding to at least one target image of a first image data group from a second image data group, which is any image data group among the plurality of second image data groups associated with the first image data group, which is any image data group among the plurality of first image data groups;
displaying a set of images of the target image and the corresponding image on a display unit in a contrastable layout;
determining whether or not a direction of image planes in the plurality of first image data groups is the same as a direction of image planes in the plurality of second image data groups; and
in a case in which the directions of the image planes of the plurality of first image data groups and the plurality of second image data groups match each other, calculating the degree of similarity.

20. A non-transitory computer-readable storage medium that stores an image diagnosis support program causing a computer to execute:
a step of acquiring a plurality of first image data groups and a plurality of second image data groups to be subjected to comparative interpretation from a data storage unit in which multiple image data groups each including a plurality of images are stored for each unit examination;
a step of associating each image data group of the plurality of first image data groups with each image data group of the plurality of second image data groups based on a degree of similarity between pieces of pixel data of each of the plurality of first image data groups and pieces of pixel data of each of the plurality of second image data groups;
a step of extracting a corresponding image corresponding to at least one target image of a first image data group from a second image data group, which is any image data group among the plurality of second image data groups associated with the first image data group, which is any image data group among the plurality of first image data groups;

a step of displaying a set of images of the target image and the corresponding image on a display unit in a contrastable layout;

a step of determining whether or not a direction of image planes in the plurality of first image data groups is the same as a direction of image planes in the plurality of second image data groups; and in a case in which the directions of the image planes of the plurality of first image data groups and the plurality of second image data groups match each other, a step of calculating the degree of similarity.

\* \* \* \* \*